(12) United States Patent
Yin et al.

(10) Patent No.: US 8,583,203 B2
(45) Date of Patent: Nov. 12, 2013

(54) FINGER TYPE PULSE AND BLOOD OXYGEN MEASURING DEVICE

(75) Inventors: Xin Yin, Nanshan Shenzhen (CN); Binbin Yan, Nanshan Shenzhen (CN); Xicheng Xie, Nanshan Shenzhen (CN)

(73) Assignee: Edan Instruments, Inc., Shekou, Nanshan Shenzhen (CN)

( * ) Notice: Subject to any disclaimer, the term of this patent is extended or adjusted under 35 U.S.C. 154(b) by 901 days.

(21) Appl. No.: 12/549,746

(22) Filed: Aug. 28, 2009

(65) Prior Publication Data

US 2011/0054280 A1    Mar. 3, 2011

(51) Int. Cl.
*A61B 5/1455* (2006.01)

(52) U.S. Cl.
USPC ............... 600/340; 600/323; 600/344

(58) Field of Classification Search
USPC ......... 600/310, 322, 323, 340, 344, 473, 476; 356/41
See application file for complete search history.

(56) References Cited

U.S. PATENT DOCUMENTS

| | | | | |
|---|---|---|---|---|
| 4,685,464 A * | 8/1987 | Goldberger et al. | ...... | 600/344 |
| 5,015,546 A * | 5/1991 | Dulaney et al. | ...... | 429/99 |
| 5,025,791 A * | 6/1991 | Niwa | ...... | 600/324 |
| 5,490,523 A * | 2/1996 | Isaacson et al. | ...... | 600/323 |
| 5,988,588 A * | 11/1999 | Allen et al. | ...... | 251/129.04 |
| 6,018,673 A * | 1/2000 | Chin et al. | ...... | 600/322 |
| 6,186,824 B1 * | 2/2001 | Lee | ...... | 439/500 |
| 2002/0043959 A1 * | 4/2002 | Tanaka et al. | ...... | 320/116 |
| 2004/0054291 A1 * | 3/2004 | Schulz et al. | ...... | 600/500 |
| 2006/0129039 A1 * | 6/2006 | Lindner et al. | ...... | 600/323 |
| 2007/0270676 A1 * | 11/2007 | Yang et al. | ...... | 600/344 |
| 2008/0183032 A1 * | 7/2008 | Hsu | ...... | 600/39 |

* cited by examiner

*Primary Examiner* — Tse Chen
*Assistant Examiner* — Chu Chuan (JJ) Liu
(74) *Attorney, Agent, or Firm* — Garcia-Zamor IP Law; Ruy M. Garcia-Zamor

(57) ABSTRACT

The invention discloses a finger type pulse and blood oxygen measuring device, including an upper shell suite and a lower shell suite that are installed with silica gel soft finger pad, and a semi-closed holding. A removable power supply module is installed in the lower shell suite. The beneficial effect of the invention is that because of the adoption of the removable type power supply module which is able to load the battery, it is easier to assemble and disassemble the battery. Additionally, the structure of the device facilitates manufacturing, enhances quality, and also increases the comfort of a person using the device.

4 Claims, 7 Drawing Sheets

FINGER TYPE PULSE AND BLOOD OXYGEN MEASURING DEVICE

TECHNICAL FIELD

The invention relates to a measuring device for diagnosis, especially refers to a finger type pulse and blood oxygen measuring device which is able to measure the blood oxygen saturation as well as the pulse rate.

BACKGROUND ART

The finger type pulse and blood oxygen measuring device is an integrated portable measuring device for the non-invasive detecting of the blood oxygen saturation and pulse rate. During the measurement, the measuring device is clipped with the finger of the patient, to collect the clinic data of the blood oxygen saturation and pulse rate for the patient. The equipment is small, portable, simple usage, and highly approbatory in the market. Currently, the finger type pulse and blood oxygen measuring device is diversiform in domestic. Chinese patent with patent number CN200610144965.3 describes a device with embossment or dent in the flank of the shell, as a marker, so as to mark the accurate measuring location conveniently; Chinese patent with patent number CN200720194193.4 describes a finger clip type blood oxygen device which is able to synchronous display the detected data, and also accurately store the data, then upload the data to computer by USB line. The current products mainly use glue poured way to encapsulate the chamber where locates the lamp-housing and photoelectric sensor in the silica gel finger pad, which increases the complicity of the manufacturing art for the finger pulse blood oxygen measuring device, and also causes bad consistency. At the same time, most of the domestic products use the battery compartment structure, and install the battery into the battery compartment which is in the inner side of the finger type pulse and blood oxygen measuring device, which causes inconvenient installation for the battery, and weakens the anti-damage of the measuring device. Therefore, the current technology still has limitation, and needs to be improved and developed.

CONTENTS OF THE INVENTION

In order to overcome the above shortage of the foresaid regular finger type pulse and blood oxygen measuring device, the invention provides a finger type pulse and blood oxygen measuring device, which is easier to assemble and disassemble the battery, and it enforces the anti-damage function of the measuring device, furthermore it simplifies the craft for the installation structure for the lamp-house and photoelectric sensor.

To achieve the above objective, the present invention adopts the following technical solution:

A finger type pulse and blood oxygen measuring device, including an upper shell suite and a lower shell suite that are installed with silica gel soft finger pad, and a semi-closed holding cavity shaped by the coordination of the silica gel soft finger pad that installed within the upper shell suite and lower shell suite; herein its feature it is that the foresaid silica gel soft finger pad that installed within the upper shell suite and lower shell suite has optical windows which are corresponding to each other, while the optical window and silica gel soft finger pad become integrated; and a removable power supply module is installed in the lower shell suite.

The foresaid upper shell suite includes an upper shell cover, a lens cover and a push-button device which is installed in the channel of the concave corresponding to the top end of the upper shell cover; the control circuit board is fixed in the inner side of the bottom of the upper shell cover by mainboard fastener.

The foresaid bottom of the control circuit board installs with optoelectronic sensors, and the top end of the circuit board installs with display screen.

The foresaid lower shell suite mainly includes silica gel soft finger pad, light emitting diode (LED) and lower shell cover; the light emitting diode (LED) is fixed in the silica gel transparent optical window which is raised in the bottom of the silica gel soft finger pad, and connects with the control circuit board, and the silica gel soft finger pad is installed in the channel of the concave of the top end of the lower shell cover.

The foresaid power supply module includes battery installation groove lid, and the battery is installed in the battery installation groove lid, while the battery installation groove and the lower shell suite is moveable mounted.

The foresaid both side of the bottom of the lower shell cover has flanging boss structure that is respectively outspread in parallel towards the interior; the battery installation groove lid is fixed in the bottom of the lower shell cover by clamping with both sides.

One end of the battery installation groove lid is closed, while the other end is open; the left and right side walls in top end of the battery installation groove lid have side walls flanging boss that is respectively outspread towards the interior.

A T type flanging boss is upwards stretching from the bottom in the middle of the battery installation groove lid, while the battery is installed in both sides of the T type flanging boss; the battery is installed in the battery installation groove lid by the coordination of a fixed clip and T type flanging boss.

In the top end of rear wall of the battery installation groove lid, by the center of T type flanging boss, two symmetric hooked flanging boss stretch upwards, while in the opening of the front end of the battery installation groove lid, an elongate cavity of a section of side wall with circular arc structure is stretching from the surface of the bottom; between two side walls of the T type flanging boss and battery installation groove lid, there are two arc shaped channel in the surface of the bottom of the battery installation groove lid.

The beneficial effects of the invention is that because of the adoption of the removable type power supply module which is able to load the battery, by the comparison with the current technology, it is easier to assemble and disassemble the battery, and it enforces the anti-damage function of the measuring device; the device also adopts the integrated technology for the mould of the transparent silica gel optical window and the silica gel soft finger pad, which makes the craft simpler, and enhances the consistency of the products, and also increases the comfort of the fingers for placement in measuring.

MODE OF CARRYING OUT THE INVENTION

Figure 1:
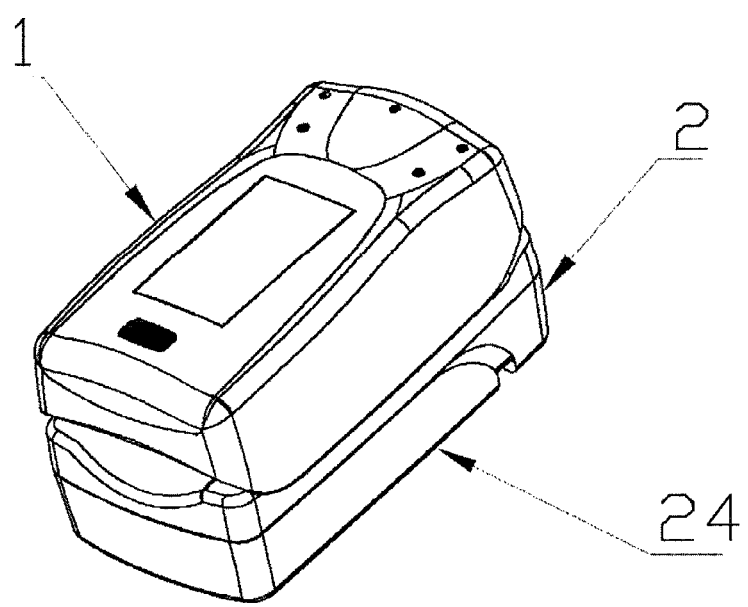
FIG. 1 is the structure figure of the invention.
Figure 2:
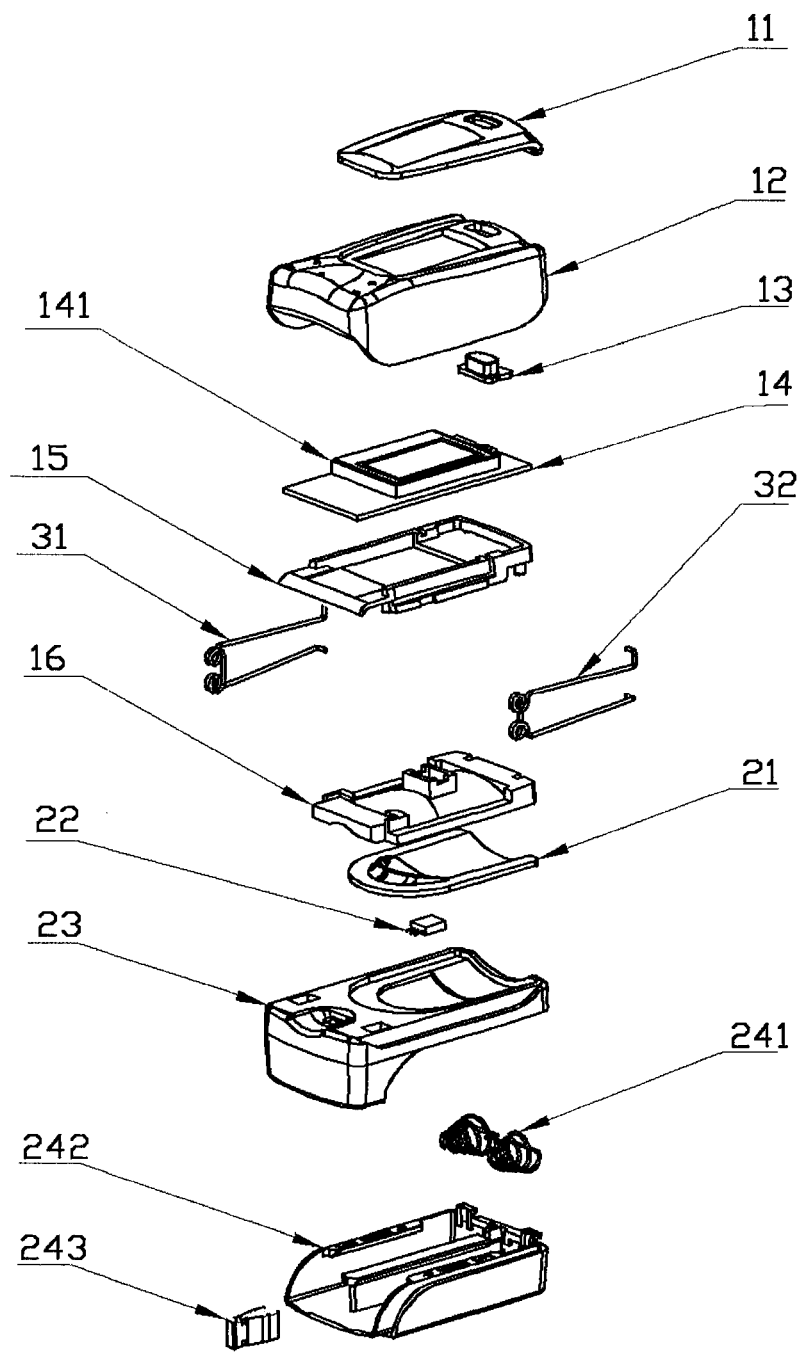
FIG. 2 is the assembly figure of the invention.

Further explanation to the invention will be stated below combining with the attached figures and the mode of carrying out the invention:

As shown in FIG. 1 and FIG. 2, a finger type pulse and blood oxygen measuring device of the invention, including an upper shell suite 1 and a lower shell suite 2; wherein the upper shell suite 1 mainly includes a lens cover 11, an upper shell cover 12, a push-button device 13, a control circuit board 14, a mainboard fastener 15 and an upper silica gel soft finger pad 16. The lens cover 11 and the push-button device 13 are installed in the channel of the concave corresponding to the top end of the upper shell cover 12; the control circuit board 14 is fixed in the inner side of the bottom of the upper shell cover 12 by mainboard fastener 15; the bottom of the control and display circuit board 14 installs with optoelectronic sensors, and the top end of the control circuit board 14 installs with display screen 141; the installation position of the display screen corresponds to the channel of the concave of the top end of the upper shell cover 12, and when the related data and figures are displaying on the display screen, the tester could see them clearly from the upward side of the lens. The silica gel soft finger pad 16 is fastened in the bottom of the mainboard fastener by sticking.

Figure 3:
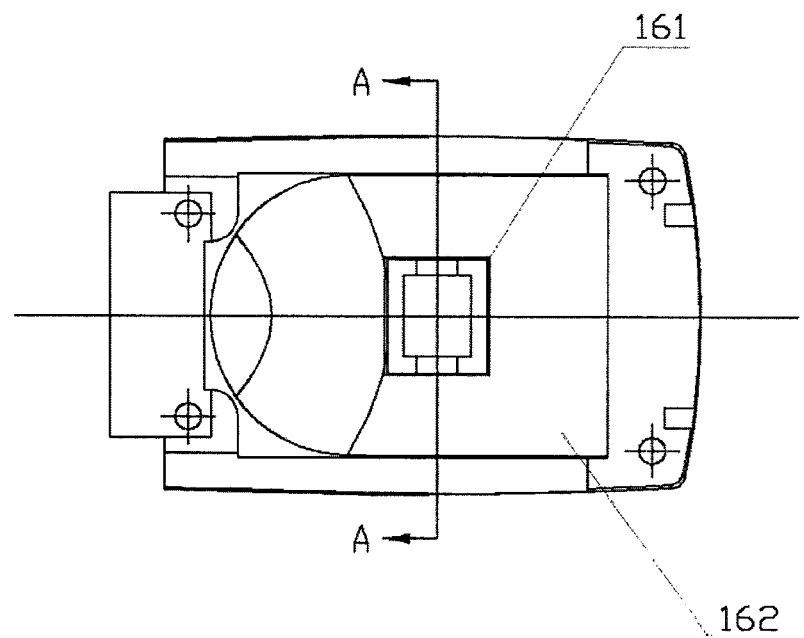
FIG. 3 is the planform of the silica gel soft finger pad that is inside the upper shell suite of the invention.
Figure 4:
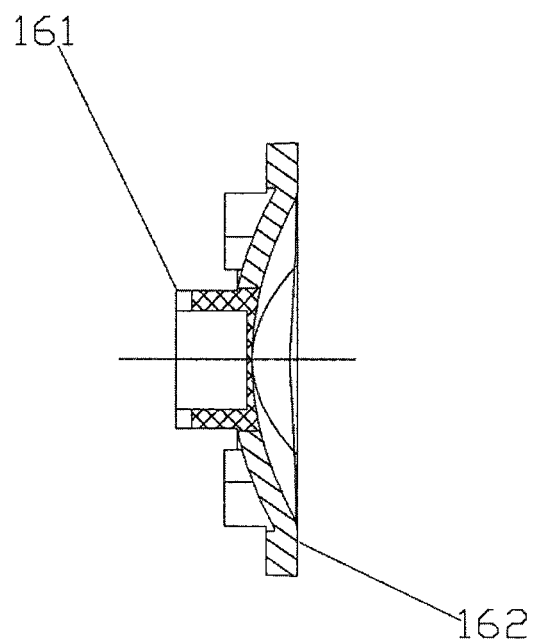
FIG. 4 is the cutaway view follows the A-A direction of the FIG. 3 of the invention.

The lower shell suite 2 includes a silica gel soft finger pad 21, a light emitting diode (LED) 22, a lower shell cover 23 and a removable power supply module 24 which is installed in the lower shell cover 23; the light emitting diode (LED) 22 is fixed in the lower silica gel transparent optical window 211 which is raised in the bottom of the silica gel soft finger pad 21 by glue poured way, and electrically connects with the control and display circuit board 14, and the lower silica gel soft finger pad 21 is installed in the channel of the concave of the top end of the lower shell cover 23 by sticking. Both side of the bottom of the lower shell cover 23 has flanging boss structure that is respectively outspread in parallel towards the interior; the battery installation groove lid 242 is fixed in the bottom of the lower shell cover 23 by clamping with both sides. As shown in FIG. 3 and FIG. 4, there is a transparent silica gel optical window 161 from the raised in the top end of the silica gel soft finger pad 16 and an arc shaped groove 162 in the bottom of the upper silica gel soft finger pad 16. The location of the raised transparent silica gel optical window 161 is corresponding to the optoelectronic sensors which is installed in the button of the control and display circuit mainboard 14 which is exactly fixed above the raised transparent silica gel optical window, so that the optoelectronic sensors is able to detect different wavelength of the ray from the lambhouse by the transparent silica gel optical window. The transparent silica gel optical window 161 and the arc shaped groove 162 use the integrated mould craft, so it is not necessary to encapsulate by glue poured.

Figure 5:
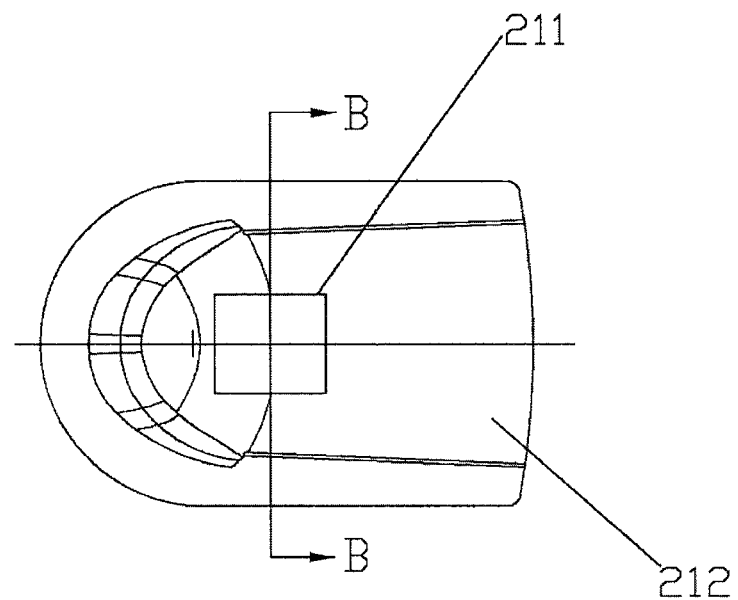
FIG. 5 is the planform of the silica gel soft finger pad that is inside the lower shell suite of the invention.
Figure 6:
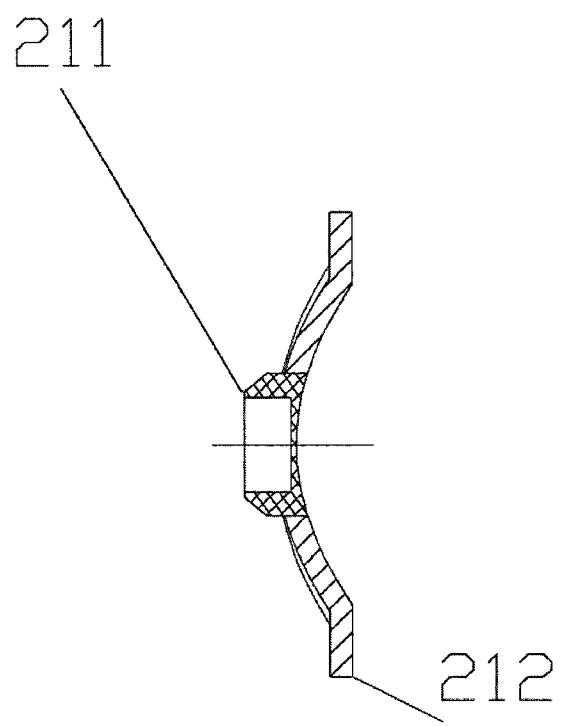
FIG. 6 is the cutaway view follows the B-B direction of the FIG. 5 of the invention.
Figure 7:
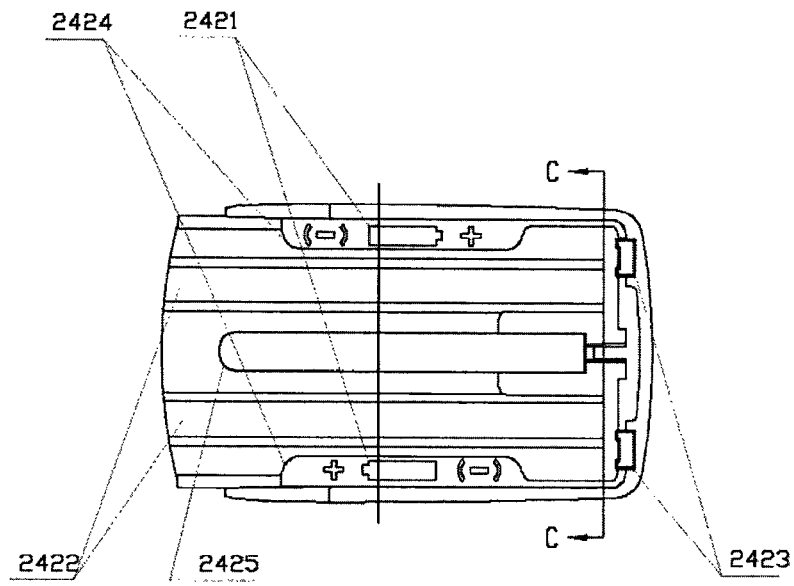
FIG. 7 is the front view of the battery installation groove lid of the invention.
Figure 8:
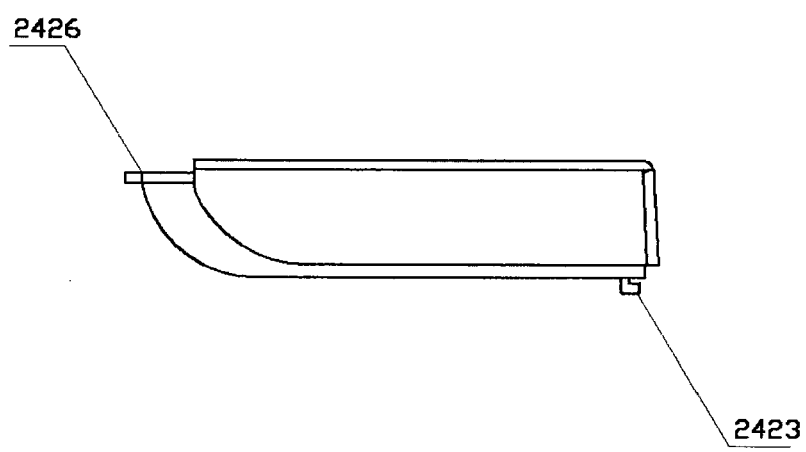
FIG. 8 is the planform of the battery installation groove lid of the invention.
Figure 9:
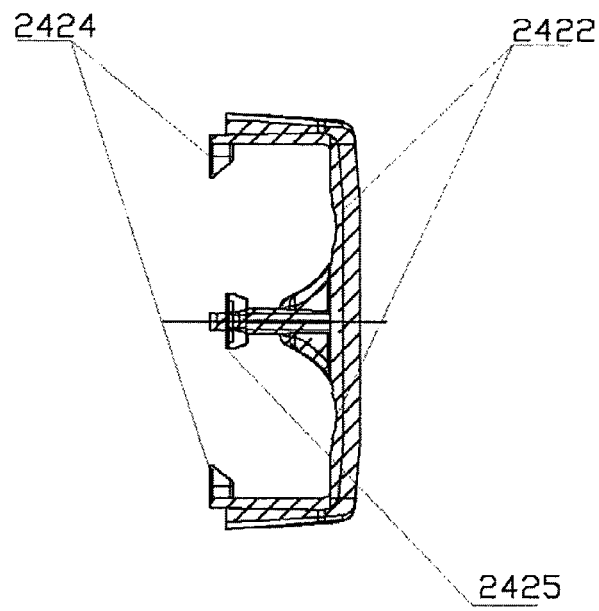
FIG. 9 is the cutaway view follows the C-C direction of the FIG. 7 of the invention.

As shown in FIG. 5 and FIG. 6, there is a transparent silica gel optical window 211 from the raised in the bottom of the silica gel soft finger pad 21 and an arc shaped groove 212 in the top end of the lower silica gel soft finger pad 21. The location of the raised transparent silica gel optical window 211 is corresponding to the raised transparent silica gel optical window 161 which is in the upper silica gel soft finger pad 16 which is exactly in the above of the raised transparent silica gel optical window 211. The transparent silica gel optical window 211 and the arc shaped groove 212 use the integrated mould craft, so it is not necessary to encapsulate by glue poured.

The connecting reposition device is composed by left connecting spring 31 and right connecting spring 32; the connecting spring is respectively clamping with the mainboard fastener 15 of the upper shell suite 1 and the lower shell cover 23 of the lower shell suite 2. The silica gel soft finger pad 16 and the silica gel soft finger pad 21 is jointly installed by the connecting reposition device, meanwhile the local of optical window in the silica gel soft finger pad 16 and the silica gel soft finger pad 21 is corresponding to each other, and together forms a half-closed holding cavity structure.

As shown in FIG. 7 to FIG. 11, the removable power supply module 24 includes a spring 241, an installation groove lid 242 and a fixed clip 243. The spring 241 is fixed in the groove of the closed end of the battery installation groove lid by clamping, and the fixed clip 243 is clamped in the outside end of the T type flanging boss 2425 of the battery installation groove lid 242. One end of the installation groove lid 242 is closed, while the other end is open, while the open end is the arc shaped structure. The left and right side walls in top end of the battery installation groove lid have side walls flanging boss 2421 that is respectively outspread towards the interior, and on both side of the flanging boss respectively has battery installation orientation mark 2424 by using injection molding; a T type flanging boss 2425 is upwards stretching from the bottom in the middle of the battery installation groove lid, and the height of the T type flanging boss is slightly lower than the flanging boss 2421 on both sides.

Between two side walls of the T type flanging boss 2425 and installation groove lid 242, there are two arc shaped channel 2422 in the surface of the bottom of the battery installation groove lid. The T type flanging boss 2425, the side wall flanging boss 2421, the arc shaped channel 2422 and the rear wall of the groove lid forms two semi-closed holding cavity. In the top end of rear wall of the battery installation groove lid, by the center of T type flanging boss 2425, two symmetric hooked flanging boss 2423 stretch upwards, while in the opening of the front end of the battery installation groove lid, an elongate cavity 2426 of a section of side wall with circular arc structure is stretching from the surface of the bottom, while the hooked flanging boss 2423 and the elongate cavity 2426 forms a clamping structure, and coordinates and fixates with the foresaid lower shell cover 23.

Figure 10:
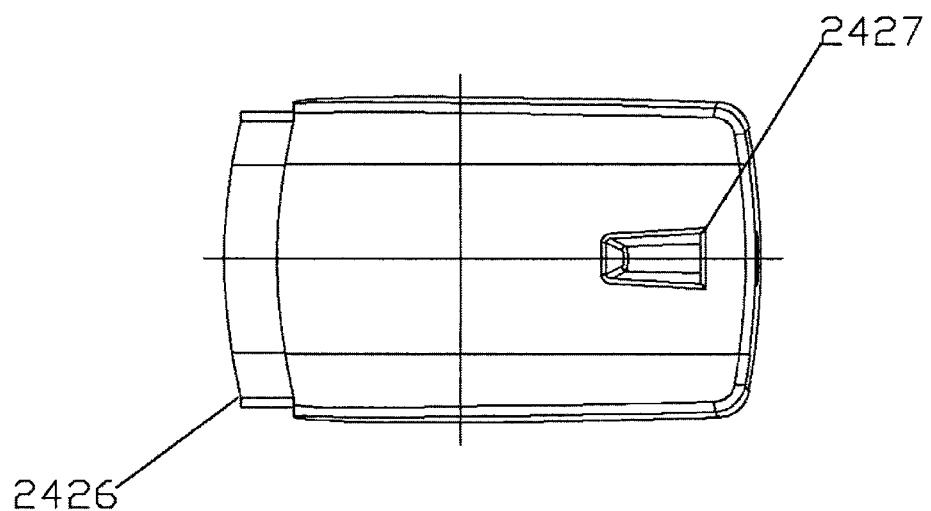
FIG. 10 is the rear view of the battery installation groove lid of the invention.
Figure 11:
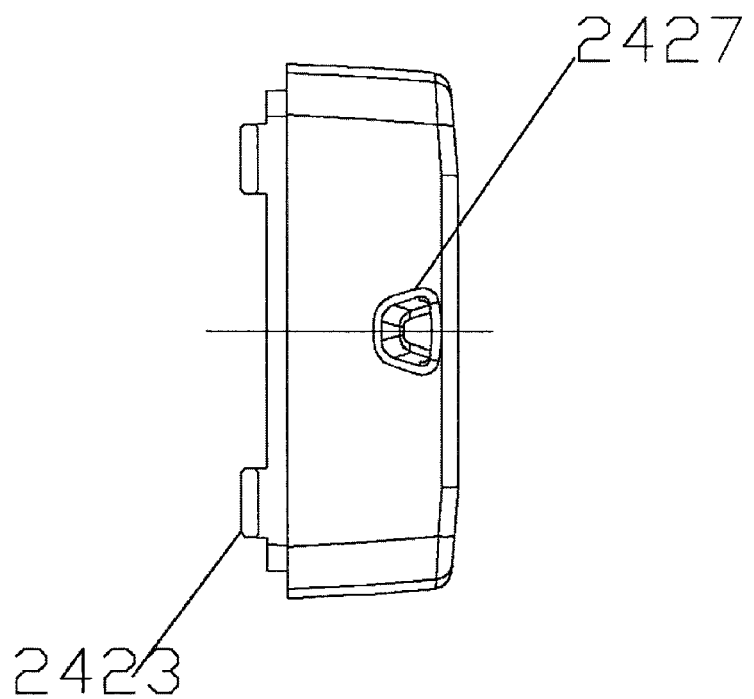
FIG. 11 is the side view of the battery installation groove lid of the invention.

As shown in FIG. 10 and FIG. 11, there is a groove 2427 in the side wall of the bottom of the battery installation groove lid 242, while inside the groove forms a through cavity that link through to the closed end of the battery installation groove lid; the groove connects with the bottom of the groove lid and the side wall of the closed end, so a hanging wire is able to be pull on, which it is convenient to carry the device.

And of course, the connecting reposition device could adopt other structures, such as tying up structure, snap-on structure and so on. Furthermore, the connecting device between the battery installation groove lid and the lower shell cover is also not limited in the clamping structure of the implantation mode, and other moveable connecting ways could be used, for example link connection.

Therefore, the implementation of the invention, is not merely limited to the above disclosed implementation mode, any theory that based on the above, and makes replacement or improvement without creative work is within the range of the implementation of the invention.

The invention claimed is:

1. A finger type pulse and blood oxygen measuring device, comprises:
an upper shell suite and a lower shell suite that are installed with silica gel soft finger pads, and a semi-closed holding cavity shaped by the coordination of the silica gel soft finger pads that are installed within the upper shell suite and the lower shell suite;
wherein the silica gel soft finger pads installed within the upper shell suite and the lower shell suite have optical windows which are opposingly aligned with respect to each other, the silica gel soft finger pads each include a transparent section of silica gel which forms the optical window resulting in the optical window and the remaining portion of the associated silica gel soft finger pad being a single silica gel member free of joints therebetween,
the optical window not being formed by a hole through the associated silica gel soft finger pad, the optical window extending completely through the associated silica gel soft finger pad, a light emitting diode is fixed on the transparent silica gel optical window of one of the silica gel finger pads, the light emitting diode being located on the side of the one silica gel finger pad on a side opposite from where the finger would make contact;
a power supply module is removably installed in the lower shell suit, wherein the power supply module is configured to hold batteries in two elongated compartments that are separate and parallel and each have two open sides when the power supply module is disconnected from the lower shell suite, a first open side of each of the two open sides of the two elongated compartments is configured to expose a lateral side of the batteries and a second open side of each of the two open sides of the two elongated compartment is configured to provide access to a terminal end of batteries when the batteries are positioned in the associated one of the two elongated compartments;
a battery installation groove lid is located on each of the two elongated compartments along the first open side to prevent batteries from falling from the power supply module while the power supply module is disconnected from the lower shell suite,
a wall between the elongated compartments has a T-shaped cross section which forms a flanging boss structure proximate the first open side and extending over a portion of the first open side of the two elongated compartments to cooperate with the respective battery installation groove lid to retain batteries in the elongated compartments when the power supply module is disconnected from the lower shell suite, wherein the battery installation groove lid located on each elongated compartment is fixed in position between the power supply module and the bottom of the lower shell cover by clamping therebetween when the battery supply module is engaged with the lower shell suite;
wherein one sidewall of each of the elongated compartments includes a circular arc structure stretching from the surface of a bottom of the power supply module along the second open side;
a fixed clip is detachably positioned on an end of the wall between the elongated compartments to prevent batteries from sliding from the power supply module through the second open side when the power supply module is detached from the lower shell suite, wherein the power supply module is configured to allow greater ease in battery changing by removal of the fixed clip and sliding out of old batteries and sliding in of new batteries without the need to pry batteries out of the power supply module.

2. The finger type pulse and blood oxygen measuring device as set forth in claim 1 characterized in that the upper shell suite includes an upper shell cover, a lens cover and a push-button device which is installed in a channel of a concave corresponding to the top end of the upper shell cover; a control circuit board is fixed in an inner side of the bottom of the upper shell cover by mainboard fastener.

3. The finger type pulse and blood oxygen measuring device as set forth in claim 2 characterized in that the bottom of the control circuit board is installed with optoelectronic sensors, and the top end of the circuit board installs with display screen.

4. The finger type pulse and blood oxygen measuring device as set forth in claim 1 characterized in that the lower shell suite mainly includes silica gel soft finger pad, light emitting diode (LED) and lower shell cover; the light emitting diode (LED) connects with the control circuit board, and the silica gel soft finger pad is installed in a channel of a concave of the top end of the lower shell cover.

* * * * *